United States Patent [19]

Gump

[11] Patent Number: 5,691,927
[45] Date of Patent: Nov. 25, 1997

[54] NUTRITIONAL AID AND METHOD OF OPERATING THE SAME

[76] Inventor: Carolyn Gump, 121 N. Fairfield St., Ligonier, Pa.

[21] Appl. No.: 296,759

[22] Filed: Aug. 26, 1994

[51] Int. Cl.⁶ .................................................. G06F 3/00
[52] U.S. Cl. ..................... 364/709.01; 364/709.03; 364/709.12
[58] Field of Search .................. 364/706, 709.01, 364/709.03, 709.14, 709.15, 413.29, 709.02, 709.12

[56] References Cited

U.S. PATENT DOCUMENTS

| | | | |
|---|---|---|---|
| 4,244,020 | 1/1981 | Ratcliff | 364/413.29 |
| 4,321,674 | 3/1982 | Krames et al. | 364/413.29 |
| 4,575,804 | 3/1986 | Ratcliff | 364/709.03 |
| 4,796,182 | 1/1989 | Duboff | 364/413.29 |
| 4,891,756 | 1/1990 | Williams, III | 364/413.29 |
| 4,894,793 | 1/1990 | Ikemoto et al. | 364/709.03 |
| 4,924,389 | 5/1990 | Gerbaulet et al. | 364/413.29 |
| 4,951,197 | 8/1990 | Mellinger | 364/413.2 |
| 4,954,954 | 9/1990 | Madsen et al. | 364/413.29 |
| 5,173,588 | 12/1992 | Harrah | 325/114 |
| 5,233,520 | 8/1993 | Kretsch et al. | 366/413.29 |

*Primary Examiner*—Chuong D. Ngo
*Attorney, Agent, or Firm*—Nils H. Ljungman and Associates

[57] ABSTRACT

An instrument, preferably hand-held and hand-operated, for quickly and efficiently assisting in the determination of important nutritional information, such as the percentage of protein, fat and carbohydrates consumed during a given period of time, as well as the total calories consumed. The instrument may preferably operate in accordance with the principle of "food exchanges" and may also preferably include a capability for precise numerical entry of various nutritional quantities. In accordance with at least one preferred embodiment of the present invention, the instrument may be shaped in the manner of a "food pyramid" and contain sections reminiscent of the sections of a typical "food pyramid".

3 Claims, 7 Drawing Sheets

NUTRITIONAL AID AND METHOD OF OPERATING THE SAME

BACKGROUND OF THE INVENTION

1. Field of the Invention

The present invention generally relates to a device for calculating absolute and/or proportional quantities for one or more nutritional categories in an individual's daily meal plan.

2. Background Information

To date, there has been thought to exist a certain degree of confusion among the general public about the tremendous variety of information that exists regarding personal nutrition. Particularly, it has been observed that much of the information disseminated today can appear conflicting and inconsistent. For example, it is believed that, for some time, there has been increasing skepticism among the general public about the success of various weight-loss plans, which are believed, by some estimates, to have a 90% fail rate. Also, by some interpretations, the general public is believed to be in the midst of developing a heightened awareness of personal physiological health, with the result that there appears to be a growing popular demand for programs, or other media, which would assist in an individual's awareness of the prevention or reduction of various diseases and other physiologically harmful phenomena.

To date, several of the dieting programs in existence have required enormous commitments of time, energy and/or personal financial resources. There has been thought to exist a growing resistance among the general populace towards such programs, which may include, among other things, eating plans, lectures or seminars, and extensive, complicated literature.

There have been proposed several solutions which have sought to relieve the health-conscious and/or nutrition-conscious individual of the numerous burdens often associated with conventional dieting programs. For example, U.S. Pat. No. 4,575,804 appears to disclose a device which provides total values of calories, carbohydrates and proteins from at least 20 food groupings, based on codes entered by the user. Apparently, the user essentially enters a code corresponding to a particular food item. Unfortunately, the codes either apparently have to be learned and memorized by the user beforehand, or they have to be searched. It appears that, on occasion, it may be necessary to sometimes make use of a weighing mechanism to accurately weigh each food item. Furthermore, the total values of each of the nutritional categories mentioned above appear to be given as an absolute value, and may be expressed, as such, in grams or other units of weight.

Thus, there appear to be several disadvantages inherent in the device disclosed in the above-cited patent and in several other known solutions. Particularly, the complexity of the programs can often be intimidating, so as to render the same generally inaccessible to the general public. The programs may often include cumbersome data banks, a search mode, and may require that procedures be learned on how to search and enter data, as well as comprehend the program. Further, with the increasing emphasis being placed today on fat consumption, several known solutions tend not to include a provision for measuring fat consumption.

U.S. Pat. No. 4,951,197 appears to disclose a device which manipulates data relating to prior personal nutritional information, body measurements and exercise levels. One of the drawbacks of this system is the apparent need for coordination with a professional dietitian. Although this known device appears to make use of predetermined percentages of various nutritional categories, it appears to be necessary that such information be presented to the user by a dietitian in a clinical setting as part of a broader weight management program.

There are other proposed solutions which appear to encompass devices which group meals by caloric content and/or store a plurality of individual food items. Such devices are generally cumbersome to hold and/or operate, and may often need to be connected to a weighing device, or relate to a specific food item. Such solutions tend to exhibit the disadvantage that they concentrate only on specific food items and, with food items changing on a virtually daily basis, these solutions may have a tendency to become obsolete relatively quickly. For the average user, the instructions, as well as the various codes which need to be entered to access the programs, can often be complicated. For many users, such solutions often appear to fail to address the issues relevant to health-conscious individuals today.

OBJECT OF THE INVENTION

With the disadvantages of known solutions discussed hereinabove, it is an object of the present invention to provide an instrument which is easy to operate, which can preferably be relatively portable, which can provide instantaneous readings of relevant nutritional information, and which can allow an individual to gain deeper knowledge about nutritional issues in general.

SUMMARY OF THE INVENTION

The above object, and others, are achieved by the present invention in that, in accordance with at least one preferred embodiment of the present invention, there is provided an instrument that can be picked up by hand and hand-held, which can be carried in a pocket or purse, and which can be used quickly and efficiently to gain results of important nutritional information, such as the percentage of protein, fat and carbohydrates consumed during a given period of time, as well as totalling all calories consumed. The calculation of the percentage of fat may, in some contexts, be particularly important, especially in light of various directives, regulations and the like which emphasize the reduction of fat in individual diets, or in institutionalized food programs, such as school lunch programs.

It is believed that, by using a device in accordance with at least one preferred embodiment of the present invention, the individual can accumulate and internalize useful knowledge about what a healthy meal plan consists of. Thus, as a result, the user can ultimately be made aware of the danger of consuming too few fruits, vegetables and fiber-rich grains as the percentage of fat increases in direct correlation to the lack of consuming foods from the fruit, vegetable and grain food categories.

The device according to the present invention, then, would appear to be capable of contributing to a healthier lifestyle without the constant need for dieting or diet plans. As such, it will be appreciated that, in accordance with at least one preferred embodiment of the present invention, the inventive device essentially does not constitute a diet plan and, in at least some respects, need not necessarily dictate the specific makeup of a user's diet. However, it is believed that the device according to the present invention can, with proper use, contribute to successful, long-term weight loss.

The capability of attaining successful, long-term weight loss can be attributed to what would appear to be an inherent educational value of the device. Particularly, through continued use, it is believed that the user can develop, over time, a heightened awareness of healthier eating.. It is believed that such an awareness can be achieved, by using the present invention, without extensive reading, research or even possibly drastic changes in one's eating habits.

In accordance with at least one preferred embodiment of the present invention, the instrument contemplated herein may preferably have the dual capability of either entering foods on the basis of the principle of "food exchanges", which tends to broadly group various foodstuffs into what is believed to be a manageable number of categories, or on the basis of direct numerical entry. In this manner, a user may take advantage of the possibility of entering nutritional quantities in a more precise manner if it is not desired, for one reason or another, to utilize the principle of "food exchanges". Both of these possibilities are discussed in detail further below.

When the word "invention" is used in this specification, the word "invention" includes "inventions", that is, the plural of "invention". By stating "invention", the Applicant does not in any way admit that the present application does not include more than one patentably and non-obviously distinct invention but that this application may include more than one patentably and non-obviously distinct invention. The Applicant hereby asserts that the disclosure of this application may include more than one invention whereby, in the event that there is more than one invention, these inventions may be patentable and non-obvious with respect to one another.

In summary, one aspect of the invention resides broadly in a device for rendering numerical manipulations of data relating to personal nutrition, the device comprising: keyboard means comprising a plurality of keys, each of the plurality of keys corresponding to a different predetermined food exchange, wherein such a food exchange corresponds to a predetermined grouping of foodstuffs; memory means for storing numerical values corresponding to a predetermined set of nutritional quantities associated with each food exchange; calculating means for rendering numerical manipulations in response to manual activation of at least one of the plurality of keys; and means for displaying at least two numerical values each corresponding, respectively, to at least two nutritional quantities, wherein one of the nutritional quantities is the approximate cumulative caloric level accumulated since a given starting time.

Another aspect of the invention resides broadly in a method of operating a device for rendering numerical manipulations of data relating to personal nutrition, such a device comprising: keyboard means comprising a plurality of keys, each of the plurality of keys corresponding to a different predetermined food exchange, wherein such a food exchange corresponds to a predetermined grouping of foodstuffs; memory means for storing numerical values corresponding to a predetermined set of nutritional quantities associated with each food exchange; calculating means for rendering numerical manipulations in response to manual activation of at least one of the plurality of keys; and means for displaying at least two numerical values each corresponding, respectively, to at least two nutritional quantities, wherein one of the nutritional quantities is the approximate cumulative caloric level accumulated since a given starting time; the method comprising the steps of: providing keyboard means; configuring the keyboard means to comprise a plurality of keys, each of the plurality of keys corresponding to a different predetermined food exchange, wherein such a food exchange corresponds to a predetermined grouping of foodstuffs; providing memory means for storing numerical values corresponding to a predetermined set of nutritional quantities associated with each food exchange; providing calculating means for rendering numerical manipulations in response to manual activation of at least one of the plurality of keys; and providing means for displaying at least two numerical values each corresponding, respectively, to at least two nutritional quantities, wherein one of the nutritional quantities is the approximate cumulative caloric level accumulated since a given starting time; the method further comprising the additional steps of: storing, with the memory means, numerical values corresponding to a predetermined set of nutritional quantities associated with a predetermined food exchange; manually activating one of the plurality of keys corresponding to the predetermined food exchange; rendering, with the calculating means numerical manipulations in response to the manual activation of the one of the plurality of keys; and displaying, with the displaying means, at least two numerical values each corresponding, respectively, to at least two nutritional quantities, wherein one of the nutritional quantities is the approximate cumulative caloric level accumulated since a given starting time.

BRIEF DESCRIPTION OF THE DRAWINGS

The embodiments of the present invention may now be understood and appreciated with reference to the accompanying drawings, wherein.

DESCRIPTION OF THE PREFERRED EMBODIMENTS

Figure 1A:
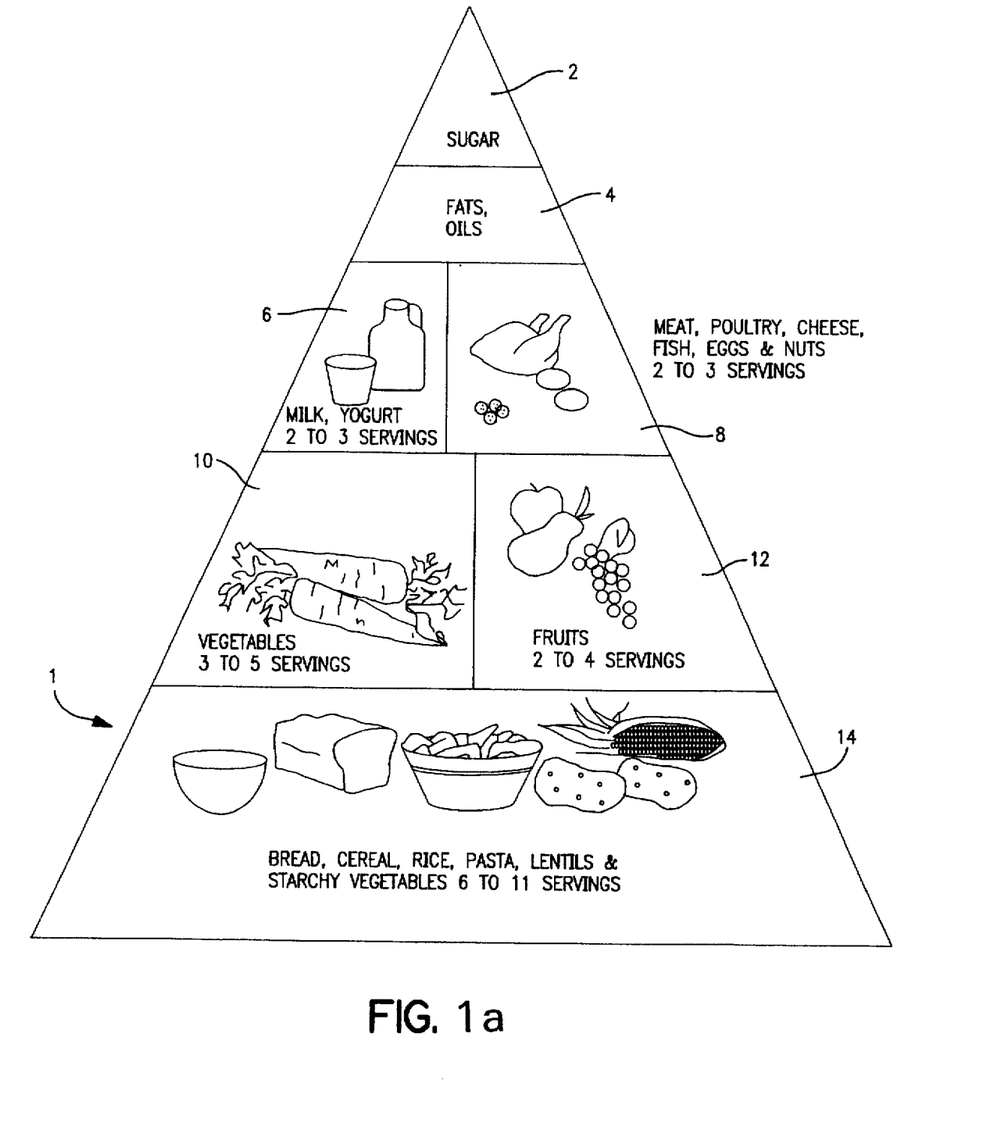
FIG. 1a illustrates a frontal view of an instrument according to the present invention.

FIG. 1a illustrates, in accordance with a preferred embodiment of the present invention, the front of an instrument 1. As shown, instrument 1 may preferably generally have the shape of a triangle, preferably an isosceles triangle. Preferably, the shape of an isosceles triangle is chosen so as to essentially correspond to what has come to be known as a "food pyramid", such as that established by the U.S. Department of Agriculture (USDA). Accordingly, the front of instrument 1 preferably sets forth, in an illustrative manner, what may be considered to be different sections of such a "food pyramid", albeit possibly modified.

In the embodiment illustrated in FIG. 1a, the upper portion of the pyramid is occupied by section 2, representing sugar, and section 4, representing fats and oils. As will be described more fully hereinbelow, sections 2 and 4 each preferably correspond to different food categories for assisting in the determination of several nutritional quantities. Although a standard "food pyramid" may typically combine sugars, fats an oils into a single category, a preferred embodiment of the present invention contemplates the separation of sugars, as a category, from fats and oils.

In an upper central section of the pyramid, on the left side, section 6, representing milk and yogurt, is preferably provided. As will be described more fully hereinbelow, section 6 preferably corresponds to a food category for assisting in the determination of several nutritional quantities.

In an upper central section of the pyramid, on the right side, section 8, representing meat, poultry, cheese, fish, eggs and nuts, is preferably provided. As will be described more fully hereinbelow, section 8 preferably corresponds to a food category for assisting in the determination of several nutritional quantities.

In a lower central section of the pyramid, on the left side, section 10, representing vegetables, is preferably provided. As will be described more fully hereinbelow, section 10 preferably corresponds to a food category for assisting in the determination of several nutritional quantities.

In a lower central section of the pyramid, on the right side, section 12, representing fruits, is preferably provided. As will be described more fully hereinbelow, section 12 preferably corresponds to a food category for assisting in the determination of several nutritional quantities.

Finally, in a lowermost section of the pyramid, section 14, representing bread, cereal, rice, pasta, lentils and starchy vegetables, is preferably provided. As will be described more fully hereinbelow, section 14 preferably corresponds to a food category for assisting in the determination of several nutritional quantities.

Preferably, in accordance with at least one preferred embodiment of the present invention, each section 2, 4, 6, 8, 10, 12 and 14 may be appropriately represented by either a pictogram, or descriptive terminology, or both. The embodiment illustrated in FIG. 1a provides one example in this regard, wherein sections 2 and 4 are provided with descriptive terminology, while sections 6, 8, 10, 12 and 14 are provided at least with pictograms. If space permits, descriptive terminology can be provided adjacent the pictograms.

It should be understood that, within the scope of the present invention, the food groups may be established in any manner, along any lines, which is deemed appropriate. In the preferred embodiment illustrated in FIG. 1a, for example, cheese has been incorporated into what is normally considered to be the "meat" group because of what are believed to be nutritional characteristics borne in common with traditional meats. Nuts and eggs have been included in the "meat" group for similar reasons. Similarly, starchy vegetables have been included in what is traditionally known as the "bread" group. As discussed above, sugar may constitute its own group, separate from fats and oils.

Although the present invention need not necessarily be limited to the "pyramid" shape illustrated in FIG. 1a, it is believed that the general similarity to the conventional USDA "food pyramid" can lend itself, on the part of a user, to a heightened awareness of the user's personal health. Particularly, it is believed that, through easy identification with a widely recognized nutritional symbol such as the USDA "food pyramid", a user may be able to more readily internalize important tenets of personal nutrition management.

FIG. 1a illustrates descriptive terminology which may be incorporated into each of the sections 2–14. Listed in conjunction with the descriptive terminology, in accordance with at least one preferred embodiment of the present invention, are indications of a recommended number of servings for each of the food groups, as generally espoused by the USDA. It is to be understood that sugar, fats and oils are recommended by the USDA to be used sparingly.

Figure 1B:
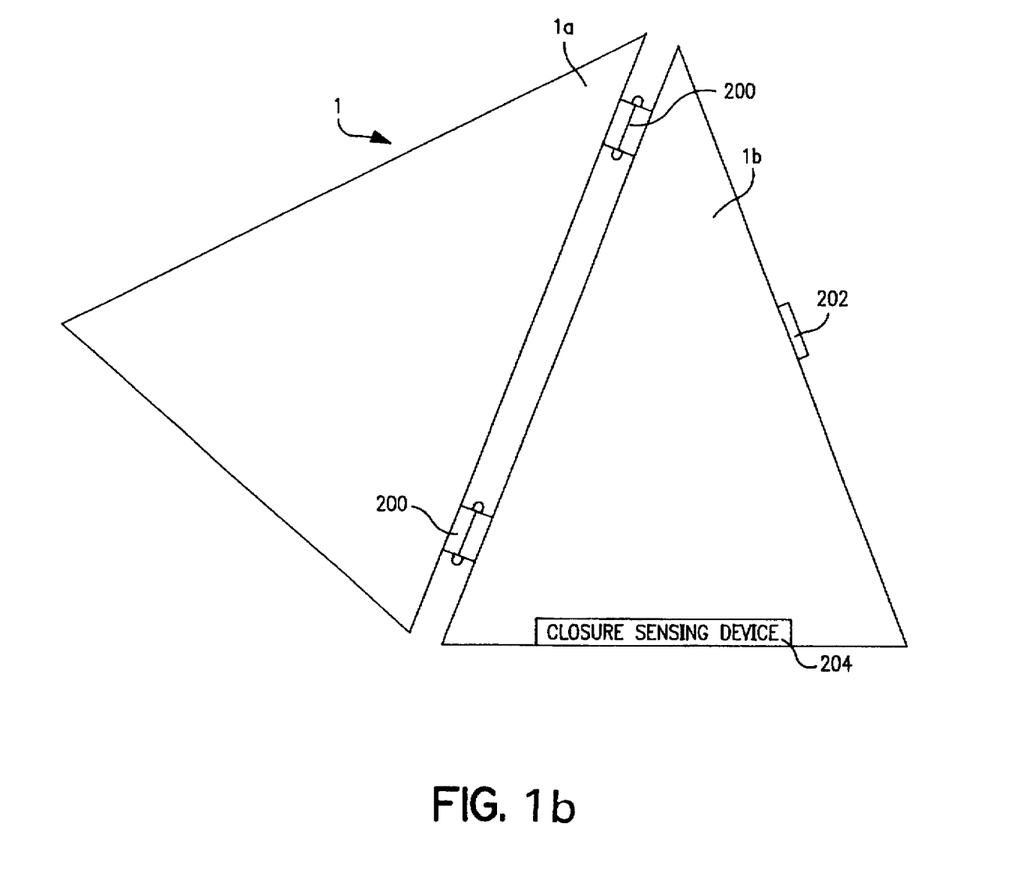
FIG. 1b schematically illustrates an opened instrument according to the present invention.

FIG. 1b schematically illustrates what may be considered to be, in accordance with at least one preferred embodiment of the present invention, a general layout for instrument 1. Particularly, in accordance with at least one preferred embodiment of the present invention, instrument 1 may preferably be constituted by halves 1a and 1b, wherein the front of left half 1a could be considered to be illustrated in FIG. 1a. A suitable hinge element or elements 200, as appropriate, may preferably be provided to render the instrument halves 1a and 1b pivotably displaceable with respect to one another, and a clasp arrangement 202 could preferably be provided to render an essentially locked or closed state of instrument halves 1a and 1b with respect to one another upon sufficient pivotal displacement of halves 1a and 1b towards one another. As will be more fully appreciated herebelow, a suitable closure sensing device 204 may preferably be provided to detect such a closed state of instrument 1, that is, of halves 1a and 1b with respect to one another. Such a closure sensing device 204 may be embodied, for example, by a solar cell, a plunger switch, a circuit arrangement, or any other electronic and/or mechanical device capable of carrying out such a function. Because such devices are generally very well known, they will not be described in further detail herein.

Figure 2:
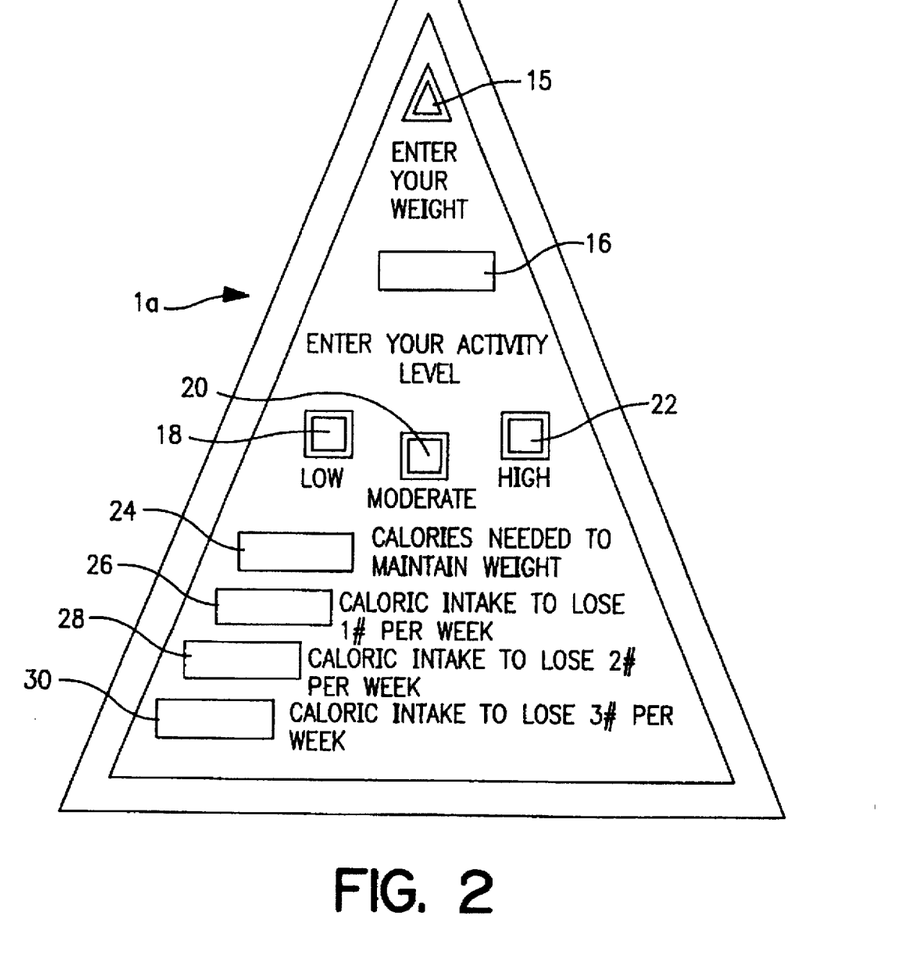
FIG. 2 illustrates the inside of the front cover of an instrument according to the present invention.

Once the instrument is opened, as shown in FIG. 1b, in accordance with at least one preferred embodiment of the present invention, as shown in FIG. 2, the inside of left half 1a may preferably contain an arrangement for entering the user's weight and activity level, for the purpose of determining various recommended caloric levels for maintaining or losing weight. Thus, in accordance with at least one preferred embodiment of the present invention, a button 15 may preferably be provided to enter, in a suitable manner, the user's weight, for display on a display area 16. As an example, button 15 could conceivably perform an iterative function, that is, in response to depression of button 15, display 16 could display a number which increases in increments of a given multiple, such as five. Conceivably, the number displayed in display 16 could increase up to a given maximum, such as about 500 or 600, before reverting to a given minimum, such as about 80 or 90.

Thence, in accordance with at least one preferred embodiment of the present invention, following entry of the user's weight, the user may then enter, preferably via one of three buttons 18, 20, 22, what the user considers to be his or her activity level which could, respectively, be considered as "low", "moderate" or "high". Consequently, in accordance with at least one preferred embodiment of the present invention, there could preferably result values displayed in display areas 24, 26, 28 and 30 which could preferably correspond, respectively, to:

a recommended daily caloric intake for maintaining the user's original weight;

a recommended daily caloric intake for losing one pound per week;

a recommended daily caloric intake for losing two pounds per week; and a recommended daily caloric intake for losing three pounds per week.

Preferably, in accordance with at least one preferred embodiment of the present invention, a "safety feature" may be built in which would advise a user against an excessively low caloric intake. Particularly, if any or all of the values displayed in areas 24–30 were to be less than a predetermined value, such as about 1200 calories, then, in accordance with at least one preferred embodiment of the present invention, where appropriate, any or all of the areas 24–30, as appropriate, could display a message such as "NO", to advise the user that the caloric level necessary for either maintaining weight or losing the indicated number of pounds is unacceptably low.

Figure 3:
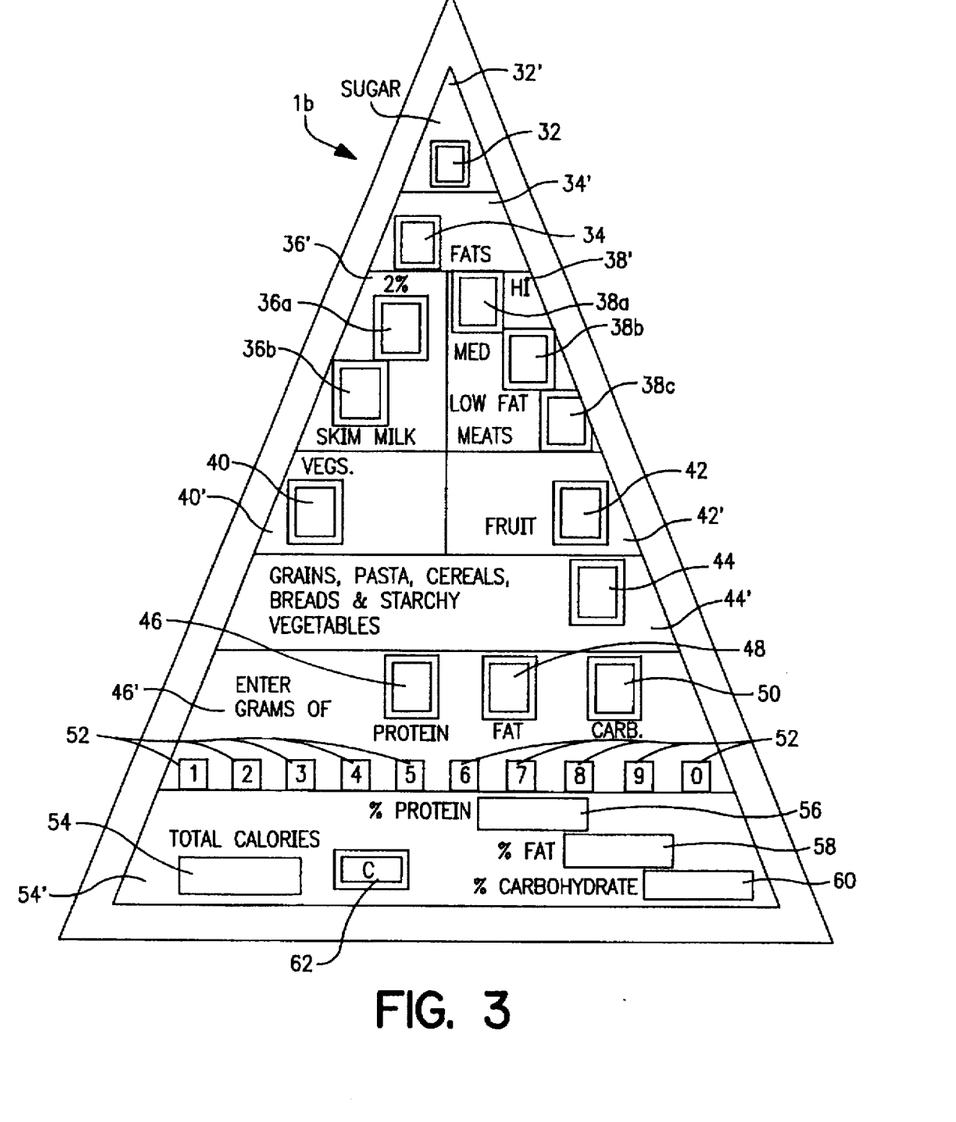
FIG. 3 illustrates the inside of the rear cover of an instrument according to the present invention.

FIG. 3 illustrates, in accordance with at least one preferred embodiment of the present invention, an arrangement for the inside of right half 1b. Particularly, as illustrated, the inside of right half 1b can preferably contain several buttons 32–52 which allow the user to input, throughout a given period of time, information relating to the foodstuffs consumed in during that period of time. In accordance with a preferred embodiment of the present invention, the buttons can preferably be divided into sections which, for the most part, can preferably correspond to the food group sections on the front of left half 1a (see FIG. 1a). Although the buttons 32–52 will now be briefly described, their function will be more apparent in the context of the method of operation discussed even further below.

Thus, in a first section 32', there may preferably a button 32 corresponding to sugars.

In a second section 34', there may preferably be a button 34 corresponding to fats and oils.

In a third section 36', there may preferably be two buttons 36a and 36b corresponding to milk, wherein button 36a could preferably correspond to "2% milk" and button 36b could preferably correspond to "skim milk".

In a fourth section 38', there may preferably be three buttons 38a, 38b and 38c corresponding to meats, wherein button 38a could preferably correspond to "high-fat meats", button 38b could preferably correspond to "medium-fat meats" and button 38c could preferably correspond to "low-fat meats".

In a fifth section 40', there may preferably be a button 40 corresponding to vegetables.

In a sixth section 42', there may preferably be a button 42 corresponding to fruits.

In a seventh section 44', there may preferably be a button 44 corresponding to grains, pasta, cereals, breads and starchy vegetables.

Optionally, in accordance with at least one preferred embodiment of the present invention, there may be an additional section 46' below the seventh section 44', which could preferably contain three buttons 46, 48 and 50 for entering specific quantities, conceivably in grams, of protein, fat and carbohydrates, respectively. Accordingly, there may preferably be provided ten numeric keys 52 to permit the user to input the specific values. This may be of use, for example, to a diabetic or other individual for whom the entry of specific quantities, to the gram, of protein, fat and carbohydrates may be desirable or necessary. This may also be of use to any individual who, for one reason or another, would wish to enter into the instrument 1 more precise information relating to nutritional quantities, such as may be found on nutrition labels of packaged foodstuffs.

In a section below either or both of the aforementioned sixth section 44' and the additional section 46', there will preferably be a display section 54' containing display areas 54, 56, 58 and 60. Preferably, in accordance with at least one preferred embodiment of the present invention, display area 54 may preferably show the accumulated total caloric value of all entries since a given starting time. Display area 56 may preferably be configured to display the percentage of the total calories accounted for by protein, display area 58 may preferably be configured to display the percentage of the total calories accounted for by fat, and display area 60 may preferably be configured to display the percentage of the total calories accounted for by carbohydrates.

Optionally, in accordance with at least one preferred embodiment of the present invention, a "clear" button 62 may preferably be provided, possibly in display section 54', to selectively revert the caloric display 54, and consequently the percentage displays 56, 58, 60, to zero. Although not illustrated, a "clear entry" button could conceivably be provided to permit the user to erase an erroneous entry.

Figure 4:
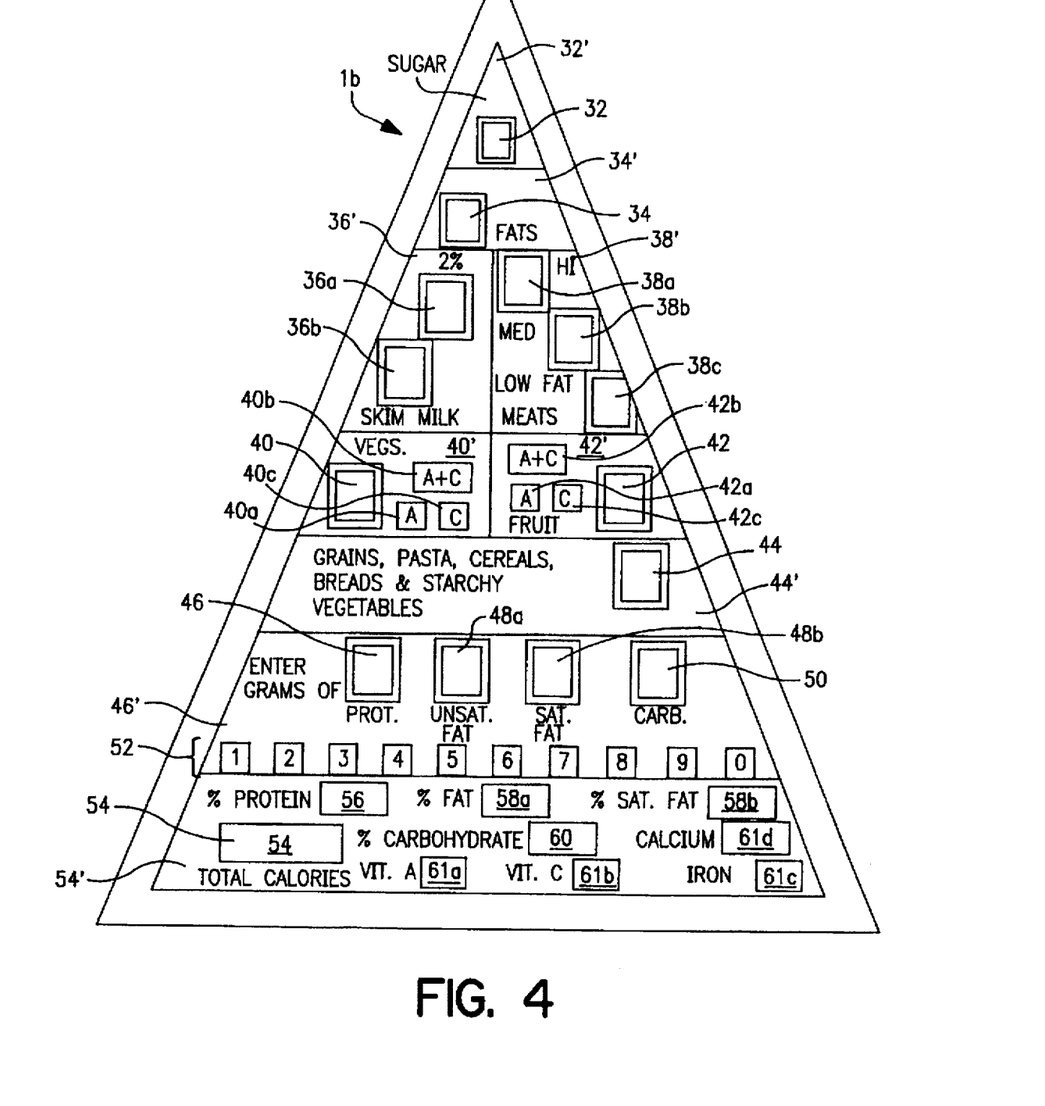
FIG. 4 illustrates an alternative embodiment of the inside of the rear cover of an instrument according to the present invention.

FIG. 4 illustrates an alternative embodiment for the right half 1b of an instrument according to the present invention. Particularly, in accordance with the embodiment illustrated in FIG. 4, section 40' may preferably include three additional buttons 40a, 40b and 40c, wherein button 40a could preferably correspond to vegetables having a significant level of Vitamin A, button 40b could preferably correspond to vegetables having a significant level of both Vitamin A and Vitamin C, and button 40c could preferably correspond to vegetables having a significant level of Vitamin C. In such a context, button 40 could preferably correspond to vegetables not having a significantly high level of either Vitamin A or Vitamin C.

Likewise, as illustrated in FIG. 4, section 42' could preferably include include three additional buttons 42a, 42b and 42c, wherein button 42a could preferably correspond to fruits having a significant level of Vitamin A, button 42b could preferably correspond to fruits having a significant level of both Vitamin A and Vitamin C, and button 42c could preferably correspond to fruits having a significant level of Vitamin C. In such a context, button 42 could preferably correspond to fruits not having a significantly high level of either Vitamin A or Vitamin C.

As illustrated in FIG. 4, section 46' could preferably include two buttons 48a and 48b corresponding to fat, as opposed to the single button 48 illustrated in FIG. 3. As such, button 48a could preferably correspond to unsaturated fat and button 48b could preferably correspond to saturated fat.

Finally, as illustrated in FIG. 4, there may preferably be provided additional display areas. Particularly, instead of the single display area 58 illustrated in FIG. 3, there may preferably be two display areas 58a and 58b, wherein display area 58a could preferably be configured to display the percentage of total calories accounted for by total fat, and display area 58b could preferably be configured to display the percentage of total calories accounted for by saturated fat. Additionally, four additional display areas 61a, 61b, 61c and 61d could preferably be configured to display, respectively, the amounts of Vitamin A, Vitamin C, iron and calcium consumed. The display amounts in areas 61a–d could preferably be shown in grams, milligrams, or any other appropriate unit of weight. Other suitable numerical values for indicating the amount of each nutrient consumed could be employed.

Although, to this point, different embodiments of an instrument according to the present invention have been described of their own accord, it is conceivable, within the scope of the present invention, to utilize the instrument in conjunction with an appropriate booklet or other suitable medium containing information, instructions, or pertinent data. As such, FIG. 5 illustrates an embodiment in which an instrument 1 according to the present invention may be utilized in conjunction with a booklet 206.

Figure 5:
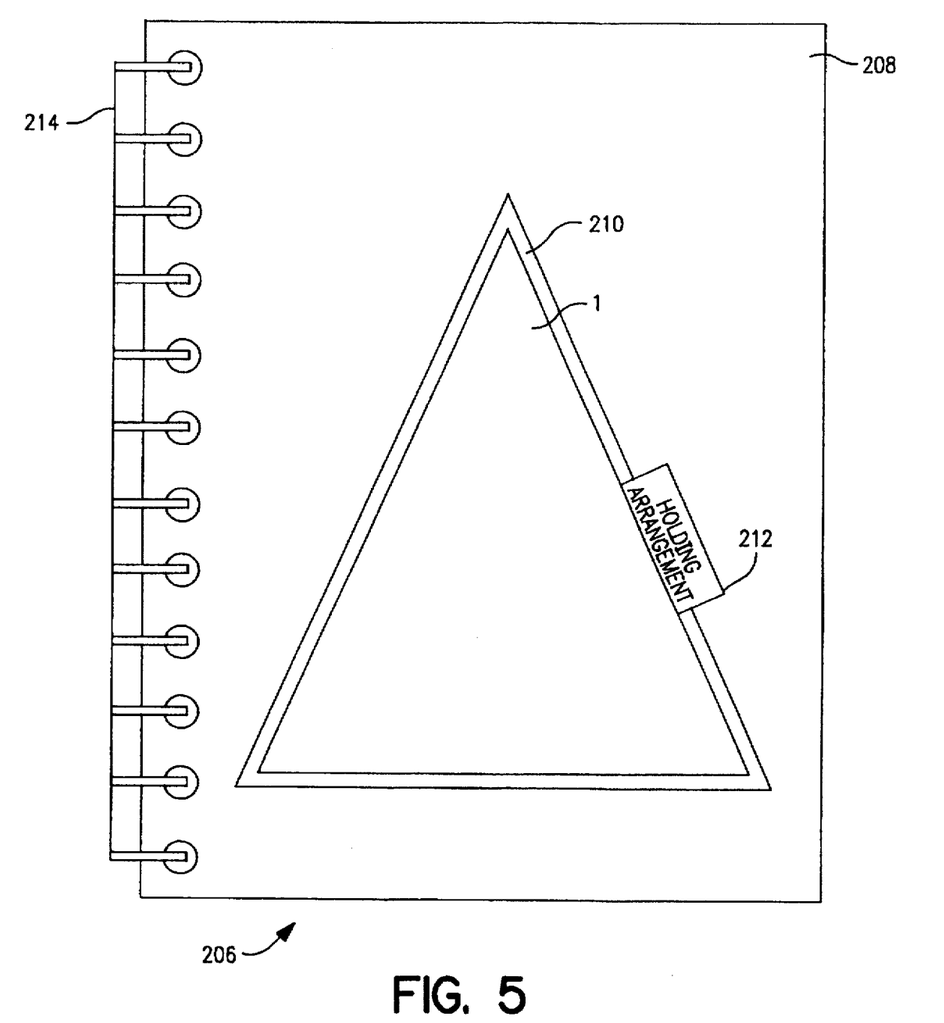
FIG. 5 schematically illustrates an embodiment of a booklet in combination with an instrument, according to the present invention.

As shown in FIG. 5, such a booklet 206 may preferably include a cover 208 containing a suitably shaped recess 210 for accommodating instrument 1. In this respect, cover 208 may conceivably be of sufficient thickness, and the recess 210 of sufficient depth, to render the instrument 1 essentially flush or slightly raised with respect to the front face of cover 208.

Preferably, there may be provided an arrangement 212 for fixedly retaining the instrument 1 with respect to cover 208, possibly with the stipulation that the instrument 1 can be optionally removed. Thus, holding arrangement 212 may preferably include a releasable clasp mechanism to provide the user with the option of either retaining the instrument 1 in the cover 208 or releasing the instrument 1 completely free from the cover 208. Conceivably, holding arrangement 212 could also be configured to optionally retain solely the right half 1b of instrument 1 (see FIG. 1b), whereby it would then be possible to still open the left half 1a of instrument 1 (see FIG. 1) for the purpose of operating instrument 1 while still being retained with respect to the cover 208. Of course, the user may still preferably have the option of removing the entire instrument 1 from the cover 208 and operating the instrument 1 independently.

It will be noted that booklet 206, apart from cover 208, may preferably contain several other pages having any information, instructions or data desired. Possibly, such a booklet 206 could be bound by a conventional spiral arrangement 214. Other possibilities for booklet 206 may include, for example, a portfolio-type arrangement. Other types of booklet arrangements are conceivable within the scope of the present invention and need not necessarily be limited to the embodiments described and/or illustrated herein.

Figure 6:
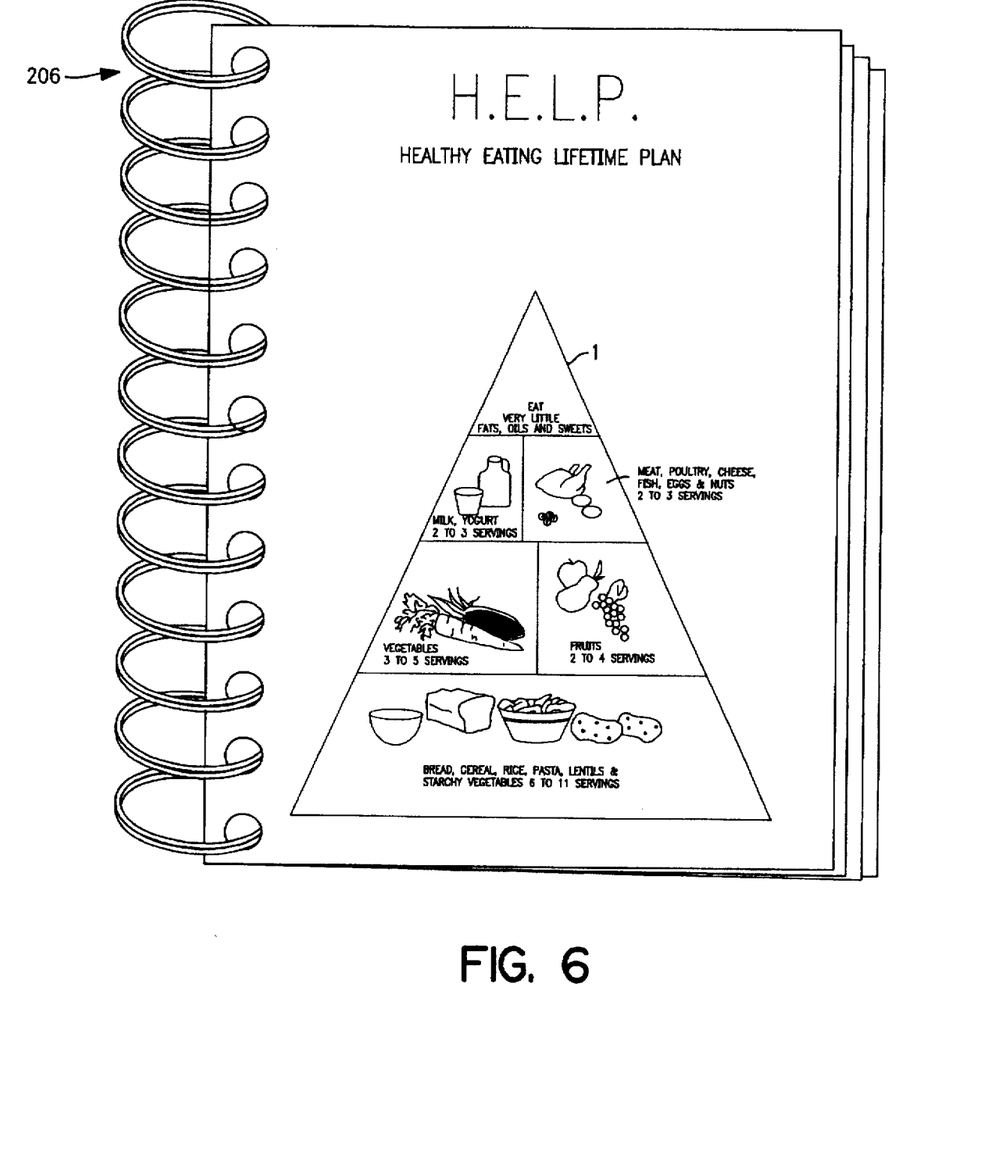
FIG. 6 provides a view of a booklet and instrument, according to the present invention.

FIG. 6 illustrates what may be considered to be a general overview of the possible appearance of a booklet 206 in combination with an instrument 1. Again, the appearance illustrated in FIG. 6 represents essentially only one possibility, and other possibilities are, of course, well within the scope of the present invention.

It should now be appreciated that if, as illustrated in FIGS. 5 and 6, an instrument 1 according to the present invention is used in conjunction with a booklet 206, there can exist a remarkable degree of flexibility for the instrument's use from the point of view of the user. Particularly, the booklet could conceivably contain the type of information, instructions, and/or data which would allow the user to fully exploit the capabilities of the instrument 1 if the user does not yet possess a significant familiarity with the makeup and functioning of the instrument 1. In time, once the user has become sufficiently familiar with the makeup and functioning of the instrument 1, he or she may optionally remove the instrument 1 from the cover 208 of the booklet 206 and carry the instrument 1 on his or her person by itself, without the booklet 206. Of course, the booklet 206 and instrument 1 can always be optionally reintegrated at the user's discretion, if the situation warrants.

Although not illustrated in FIGS. 5 and 6, the cover 208 of booklet 206 could conceivably contain elements which would allow the instrument 1 to be recharged in between periods of use. In such an instance, cover 208 could preferably be provided with an appropriate outlet for an electrical adapter, and recess 210 could preferably be provided with conventional electrical contacts, capable of being interfaced with instrument 1, to recharge instrument 1. Generally, recharging arrangements are well-known and, as such, will not be described further herein.

Some possible dimensions associated with instrument 1 and booklet 206 will now be discussed briefly. Particularly, instrument 1 will preferably be sized so as to be able to be carried in one's pocket or purse. In this respect, for example, instrument 1 may preferably have a size on the order of magnitude of a standard, hand-held calculator. As an example, an instrument 1, if generally in the shape of an isosceles triangle, may preferably have a dimension of about 3 inches to about 5½ inches at the base of the triangle, with a vertical dimension, from base to vertex, of about 3¾ inches to about 7⅛ inches. The ratio of base to height may preferably be between about 0.7 and about 0.85. The thickness of the instrument 1 and of constituent halves 1a and 1b may preferably be as reduced as technology will allow.

It is conceivable, in accordance with at least one alternative embodiment of the present invention, that instrument 1 not be shaped in the manner of an isosceles triangle. It is conceivable, for example, for instrument 1 to have the general shape of a rectangle. Conceivably, the "food pyramid" arrangement could still be inlaid or imprinted upon such a rectangular shape or any other shape which may be employed.

In accordance with at least one preferred embodiment of the present invention, booklet 206 may preferably be sized so as to adequately accommodate instrument 1 without being excessively bulky such that, for example, the ensemble of booklet 206 and instrument 1 may be easily carried in a purse or briefcase. In this respect, booklet 206 may, for example, conceivably have rectilinear dimensions of between about 5"×6" to about 7"×9".

The disclosure now turns to a discussion, in accordance with at least one preferred embodiment of the present invention, of the functioning of an instrument according to the present invention. As such, reference will be made to any or all of the FIGS. 1a–6.

Generally, in accordance with at least one preferred embodiment of the present invention, instrument 1 can be considered to be operable in connection with the principle of "food exchanges". As such, the principle of "food exchanges" can generally be thought of as the interchangeability of foodstuffs having similar nutritional and/or caloric values.

It is believed that this general principle of "food exchanges" can, in the context of the present invention, provide for a significantly simple and easy-to-learn arrangement for entering the types of foodstuffs that the user may consume over a given period of time.

Therefore, it is to be understood that, in accordance with at least one preferred embodiment of the present invention, instrument 1 can essentially be thought of as having a manageably small number of buttons with which a user can record the types of foodstuffs that he or she consumes. By broadly grouping different foodstuffs into a manageable number of categories through the principle of "food exchanges", the number of procedural steps required to operate the instrument 1 can be significantly small.

With the foregoing in mind, the disclosure will now turn to a typical sequence of operations, in accordance with at least one preferred embodiment of the present invention, of an instrument 1, and embodiments thereof, such as that illustrated in FIGS. 1a–6.

With reference to FIG. 1a, as stated further above, the instrument 1 preferably contains a set of sections 2–14 on the front face of the instrument 1, each preferably containing pictograms and/or descriptive terminology. It will be appreciated, then, that, in such a context, it is conceivable to provide any desired visual emphasis through use of different colors, patterns, shades, etc. It is conceivable, and even desirable, to employ particularly striking color schemes and iconographic arrangements which can assist the user in his or her identification and/or appreciation of the various food groups. Further, in view of the preferred layout of the inside portion of the right half 1b of instrument 1 (see FIGS. 3 and 4), it is conceivable that an appropriately decorated front face of the instrument 1 will assist in the user's identification and appreciation of the sections 32'-44' when it is desired to operate the instrument 1.

Upon opening the instrument 1, preferably in the manner illustrated in FIG. 1b, in accordance with at least one preferred embodiment of the present invention, either of the inside portions of halves 1a and 1b will be immediately available to the user for operation. Preferably, hinge element(s) 200 may, in a known manner, be so arranged as to permit halves 1a and 1b to pivotally displace with respect to one another only over a fixed angle of displacement such that, for example, they will not be able to displace beyond about 180° with respect to one another.

Generally, it may be desired that a user will wish to operate the instrument, with the purpose of totalling caloric intake and determining other nutritional quantities, such as the percentage of consumed calories accounted for by fat, over a fixed period of time, such as one day. Prior to undertaking such an operation, however, the user may wish to generate basic caloric guidelines for any weight-related goals he or she may have.

Thus, the user may essentially enter his or her weight, conceivably via button 15, followed by his or her activity level, via one of the buttons 18-22, with the result that appropriate caloric levels will be displayed in display areas 24-30, as discussed further above.

It will be understood that, in accordance with at least one preferred embodiment of the present invention, in order for such calculations to be rendered, the instrument 1 will preferably be provided with appropriate circuitry and memory. Preferably, the instrument 1 may have a capability for being selectively pre-programmed, either at the factory or by the user, in order to undertake the numerical manipulations desired. In the case of the embodiment illustrated in FIG. 2, it is to be understood that, generally, there have been established several conventionally accepted guidelines for determining the effect of a "low", "moderate", or "high" activity level on weight reduction, as well as for the quantity of calories necessary for losing one, two or three pounds of body weight in one week. The type of circuitry and memory necessary to undertake numerical manipulations such as those contemplated in accordance with the embodiment of FIG. 2 would appear to be quite well-known. The terminology "low", "moderate" and "high", as applied to activity level, may preferably be utilized along what are believed to be conventional guidelines such that, for example, "low" may be indicative of a generally sedentary activity level, with little exercise; "high" may be indicative of a highly active level of exertion on a regular basis, such as a daily program of vigorous exercise; and "moderate" may be indicative of a moderate level of exercise, such as a program of exercise carried out a few times a week with moderate exertion.

Subsequently, with reference now to FIG. 3, when the user wishes to initiate his or her fixed period of diet monitoring, he or she may preferably revert the displays in section 54' to zero, conceivably via the aforementioned "clear" button 62. Thence, in accordance with at least one preferred embodiment of the present invention, it is contingent upon the user to record his or her intake of foodstuffs by way of buttons 32-44, and optionally buttons 46-52.

At this juncture, one possibly significant function of the booklet 206 illustrated in FIGS. 5 and 6 will become apparent. Particularly, in accordance with at least one preferred embodiment of the present invention, booklet 206 may preferably contain information relating to appropriate groupings of various foodstuffs in accordance with the aforementioned principle of "food exchanges". Thus, in accordance with at least one preferred embodiment of the present invention, each of the buttons 32-44 may essentially be considered as each corresponding to a different food grouping, wherein various foodstuffs falling under the scope of each food grouping may be enumerated in the booklet 206. Over time, in accordance with at least one preferred embodiment of the present invention, a user should essentially be able to internalize the makeup of each of the food groupings corresponding to each button 32-44 and may be able to use the instrument 1 without the booklet 206.

Accordingly, whether or not the booklet 206 is present, in accordance with at least one preferred embodiment of the present invention, the user will, upon consumption of a particular foodstuff, press the appropriate button 32-44 corresponding to the food grouping which encompasses the consumed foodstuff. Preferably, in accordance with at least one preferred embodiment of the present invention, if the foodstuff in question is the first foodstuff consumed in the prescribed period of time, the approximate caloric value of the foodstuff will be shown in display area 54, while the percentage values of protein, fat and carbohydrate will preferably be shown in display areas 56, 58 and 60, respectively.

Accordingly, as the user consumes subsequent foodstuffs during the prescribed period of time, the values shown in display areas 54-60 will preferably be cumulative, that is, be indicative of the totality of foodstuffs consumed up to that point.

Preferably, in accordance with at least one preferred embodiment of the present invention, if section 46' is included as part of the instrument 1, the user may enter, to the gram, any known quantities of protein, fat or carbohydrate consumed in conjunction with a particular foodstuff. This option may be desired if a user does not want to rely entirely on the principle of "food exchanges" for entering and monitoring nutritional quantities. Conceivably, operation of buttons 46-52 could involve an initial numerical entry with buttons 52, followed by depression of one of the buttons 46-50, wherein the latter step would confirm entry of the initial numerical value into the instrument's circuitry.

It is to be understood that an instrument 1 having a right half 1b such as that illustrated in FIG. 4 will, in accordance with at least one preferred embodiment of the present invention, preferably be operable in essentially the same manner as just described with relation to FIG. 3. Thus, for example, in the context of the embodiment of FIG. 4, it is to be understood that the buttons 40a–c and 42a–c, relating to Vitamins A and C, would essentially merely constitute additional food groupings.

It should be understood that, in accordance with at least one preferred embodiment of the present invention, in order for the calculations described with relation to FIGS. 3 and 4 to be rendered, the instrument 1 will preferably be provided with appropriate circuitry and memory. Preferably, the instrument 1 may have a capability for being selectively pre-programmed, either at the factory or by the user, in order to undertake the numerical manipulations desired. In the case of the embodiments illustrated in FIGS. 3 and 4, it is to be understood that, generally, by way of the "food exchange" principle, there have been established several conventionally accepted guidelines for determining the caloric quantities and other nutritional information corresponding to each of the food groupings contemplated herein.

The type of circuitry and memory necessary to undertake numerical manipulations such as those contemplated in accordance with the embodiments of FIGS. 3 and 4 would appear to be quite well-known. It is to be understood that, in accordance with at least one preferred embodiment of the present invention, such circuitry and memory can be reprogrammable so as to be adaptable to a wide variety of contexts.

The disclosure now briefly turns to a discussion of possible types of numerical manipulations which may be undertaken by an instrument 1 in accordance with the present invention. For this example, reference can be made to FIG. 3. To begin with, the instrument 1 may conceivably have following values in memory:

TOTCAL, TOTPRO, PERPRO, TOTFAT, PERFAT, TOTCAR and PERCAR, which could correspond, respectively, to: the total cumulative calories (as displayed in area 54), the number of calories of TOTCAL accounted for by protein, the percentage of total calories accounted for by protein (as displayed in area 56), the number of calories of TOTCAL accounted for by fat, the percentage of TOTCAL accounted for by fat (as displayed in area 58), the number of calories of TOTCAL accounted for by carbohydrates, and the percentage of TOTCAL accounted for by carbohydrates (as displayed in area 60); and $CAL_i$, $PRO_i$, $FAT_i$ and $CAR_i$, which could correspond, respectively, to: the number of calories accounted for by a serving of a food exchange i, the number of calories of $CAL_i$ accounted for by protein, the number of calories of $CAL_i$ accounted for by fat, and the number of calories of $CAL_i$ accounted for by carbohydrates; wherein i=1 ... n and n=the number of "food exchanges" available for use by in conjunction with the instrument 1.

Thus, for example, in response to the activation of one of the food exchange buttons, such as, for example, button 42 (corresponding to fruits), and if it is to be assumed that, for the fruit exchange, i=9, then the following numerical manipulations may then conceivably be undertaken by the circuitry of the instrument 1:

TOTCAL=TOTCAL+$CAL_9$;
TOTPRO=TOTPRO+$PRO_9$;
TOTFAT=TOTFAT+$FAT_9$;
TOTCAR=TOTCAR+$CAR_9$;
PERPRO=100*TOTPRO/TOTCAL;
PERFAT=100*TOTFAT/TOTCAL; and
PERCAR=100*TOTCAR/TOTCAL;

whereby the revised values for TOTCAL, PERPRO, PERFAT and PERCAR will preferably be displayed, respectively, in areas 54, 56, 58 and 60.

It is to be understood that the embodiment illustrated in FIG. 4, as well as other embodiments contemplated by the present invention, can preferably operate under similar principles with only minor modifications.

It is to be understood that the numerical entry keys 46, 48, 50 and 52 contained in section 46' could, conceivably, result in direct entry of values $PRO_X$, $FAT_X$, and $CAR_X$ into instrument 1, for direct use in the numerical manipulations listed above, whereby X corresponds to a foodstuff selected by the user, for which precise nutritional information is readily available, and whereby there would essentially be no need for the instrument 1 to recall any values $PRO_i$, $FAT_i$ or $CAR_i$ stored in memory.

In accordance with at least one preferred embodiment of the present invention, a closure sensing device 204, such as that described and illustrated further above with relation to FIG. 1b, could preferably be employed so as to perform any one of a desired number of functions upon closure of the instrument 1. For example, in accordance with at least one preferred embodiment of the present invention, all values displayed in displays 24-30 and/or 54-60 could preferably be retained in memory in response to closure of the instrument 1 and possibly erased from the displays 24-30 and/or 54-60, until such a time that, conceivably, the user touches one or more buttons to reinitiate the cumulative calculation mode of the instrument.

In general recapitulation, the present invention can essentially be thought of as responding to a need for a simple means for immediately calculating the percentage of protein, fat and carbohydrate, or other quantities, in an individual's daily meal plan.

It will be appreciated that, in accordance with at least one preferred embodiment of the present invention, a user can immediately be cognizant of pertinent nutritional recommendations from the American Heart Association, the American Diabetes Association, the American Cancer Association, the USDA, the Human Nutrition Information Service and many other organizations, whose guidelines could conceivably be followed in conjunction with the present invention. Conceivably, for example, the present invention could be employed to help ensure that a user does not exceed a particular percentage value of fat in a given day, such as about 30%, to encourage the user to develop a meal plan rich in grains, vegetables and fruits.

Preferably, in accordance with at least one preferred embodiment of the present invention, the types of hand held instrument contemplated herein may be made of an appropriately durable material, such as lucite plastic.

It is believed that the division of food groups contemplated herein, particularly that described and illustrated with relation to FIG. 1a, is significantly closely related to the food groups suggested by the "United States Food Exchanges" and the "American Diabetic Exchange System".

It will be appreciated that the "pyramid" shape of the instrument 1 contemplated herein, with the corresponding food groups, has, by many interpretations, been recognized as a universal symbol of food groups to be utilized on a national scale, as apparently stipulated by the USDA and the Human Nutrition Service. It will also be appreciated that, to date, it is believed that the "pyramid" symbol has been used on many food boxes, has been widely taught in schools and, accordingly, has essentially been "marketed" in such a manner as to have already likely developed a significant public awareness of the meaning of the "pyramid".Symbol and recognition of the foods belonging to the constituent categories.

The general simplicity of embodiments of the present invention will be appreciated in that, by simply touching a given button, the quantities relating to the corresponding food grouping are automatically entered into the user's meal plan and that results appear virtually instantly, showing: the total calories; the percentage of calories from protein, fat and carbohydrates; and possibly other quantities, as well. It will be appreciated that subsequent entries will result in essentially instant changes in the displays.

It will be appreciated that, in accordance with at least one preferred embodiment of the present invention, should the user not be immediately aware of which button to press, a booklet, such as the booklet 206 described heretofore, can be consulted.

With reference to FIGS. 3 and 4, it will be appreciated that the buttons in section 46' can be utilized in conjunction with corresponding nutritional information provided on labels and products, especially in the case of "combination foods", wherein there may be some uncertainty as to which food grouping a particular foodstuff may fall within. It is believed that many restaurants, including fast-food restaurants, can also provide such nutritional information.

Preferably, in accordance with at least one preferred embodiment of the present invention, the inside of right half 1b of instrument 1, as illustrated in FIGS. 3 and 4, may be color-coded to distinguish each of the sections 32'-44' from one another.

Conceivably, an instrument 1 according to the present invention could be utilized in a manner wherein entering a foodstuff will show the potential result of ingesting the foodstuff. If the result of eating such a foodstuff will undesirably elevate the cumulative percentage of fat, then the user can choose an alternate food, or perhaps choose to add fruits, vegetables, grains or starches containing no fat, in order to determine whether the fat percentage would be reduced to an acceptable level. In such instances, it may be desirable to provide the instrument with a "clear entry" button, as discussed earlier.

Further, it is conceivable, within the scope of the present invention, to enable instrument 1 to be selectively switched between an operating mode and a test mode. In the test mode, the user could conceivably enter different types of foodstuffs in order to determine the potential effect of certain foodstuffs on the values of calories, fat, etc. already cumulatively calculated up to that point. Thus, with the day's values already determined up to that point, the user may conceivably switch to the "test" mode and render entries, based on the potential of consuming certain foodstuffs, to determine what the resultant cumulative calories, fat, etc., for the day would be. Having done this, the user would then conceivably be able to switch back to the normal operating mode to continue the legitimate entry of foodstuffs into the instrument 1 and resume the cumulative tallying described herein. Switching between a "test" mode and a "normal operating" mode could conceivably be undertaken by any appropriate means, such as by way of a switch provided on the instrument, or by way of another button provided on the instrument.

It will be appreciated that, in accordance with at least one preferred embodiment of the present invention, the need to memorize calories, fat grams, or any other nutritional information for the purpose of maintaining a healthy eating plan, will essentially be precluded.

It will be appreciated that diabetics could conceivably benefit from the present invention by incorporating the same into their diabetic eating plan and/or consulting with a dietitian. The reduction of fat for a diabetic will help prevent the serious side effects that may result from a diet too high in fat.

One highly desirable goal of healthier eating is to reduce the intake of fat to below 30%. It would appear, by some interpretations, that a highly desirable way to accomplish this goal is to add grains, fruits and vegetables to the meal plan. It will be understood that, essentially, such foods generally contain little or no fat, but will essentially supply added minerals and vitamins for optimum health.

It will be understood from the disclosure hereinabove that variations could be made to the described and illustrated embodiments without departing from the scope of the invention. For example, even though the embodiments of the present invention have generally been illustrated and described with relation to the shape of a "food pyramid", it is conceivable to utilize other shapes while still retaining essentially the same functions. Particularly, for example, it is conceivable to render an essentially circular shape for the instrument 1 so that the instrument 1 could essentially be reminiscent of a compact. Other possible shapes for instrument 1, among others, would be square, rectangular, hexagonal and octagonal.

Within the scope of the present invention, other types of nutritional information could conceivably be displayed for the user, such as quantities of vitamins and minerals not specifically described herein.

All, or substantially all, of the components and methods of the various embodiments may be used with at least one embodiment or all of the embodiments, if any, described herein.

All of the patents, patent applications and publications recited herein, if any, are hereby incorporated by reference as if set forth in their entirety herein.

The details in the patents, patent applications and publications may be considered to be incorporable, at applicant's option, into the claims during prosecution as further limitations in the claims to patentably distinguish any amended claims from any applied prior art.

The appended drawings, in their entirety, including all dimensions, proportions and/or shapes in at least one embodiment of the invention, are, if applicable, accurate and to scale and are hereby incorporated by reference into this specification.

The invention as described hereinabove in the context of the preferred embodiments is not to be taken as limited to all of the provided details thereof, since modifications and variations thereof may be made without departing from the spirit and scope of the invention.

What is claimed is:

1. A device for rendering numerical manipulations of data relating to personal nutrition, said device comprising:

first keyboard means, said first keyboard means comprising a plurality of keys, each of said plurality of keys corresponding to a different predetermined food exchange, wherein such a food exchange corresponds to a predetermined grouping of foodstuffs;

memory means for storing numerical values corresponding to a predetermined set of nutritional quantities associated with each food exchange;

first calculating means, said first calculating means having means for rendering numerical manipulations in response to manual activation of at least one of said plurality of keys of said first keyboard means;

first means for displaying, said first means for displaying having means for displaying at least two numerical values each corresponding, respectively, to at least two nutritional quantities, wherein one of said nutritional quantities is the approximate cumulative caloric level accumulated since a given starting time;

second keyboard means, said second keyboard means comprising a plurality of keys;

second calculating means, said second calculating means having means for rendering numerical manipulations in response to manual activation of at least one of said plurality of keys of said second keyboard means;

each of said plurality of keys of said second keyboard means being configured to enter, into said second calculating means, at least a user's weight; and second displaying means, said second displaying means having means for displaying at least one numerical value corresponding at least to a recommended daily caloric intake for losing a predetermined amount of weight per week.

2. A method of operating a device for rendering numerical manipulations of data relating to personal nutrition, such a device comprising: first keyboard means, said first keyboard means comprising a plurality of keys, each of said plurality of keys corresponding to a different predetermined food exchange, wherein such a food exchange corresponds to a predetermined grouping of foodstuffs; memory means for storing numerical values corresponding to a predetermined set of nutritional quantities associated with each food exchange; first calculating means, said first calculating means having means for rendering numerical manipulations in response to manual activation of at least one of said plurality of keys of said first keyboard means; first means for displaying, said first means for displaying having means for displaying at least two numerical values each corresponding, respectively, to at least two nutritional quantities, wherein one of said nutritional quantities is the approximate cumulative caloric level accumulated since a given starting time; second keyboard means, said second keyboard means comprising a plurality of keys; second calculating means, said second calculating means having means for rendering numerical manipulations in response to manual activation of at least one of said plurality of keys of said second keyboard means; each of said plurality of keys of said second keyboard means being configured to enter, into said second calculating means, at least a user's weight; second displaying means, said second displaying means having means for displaying at least one numerical value corresponding at least to a recommended daily caloric intake for losing a predetermined amount of weight per week; said method comprising the steps of:

provide first keyboard means;

configuring the first keyboard means to comprise a plurality of keys, each of said plurality of keys corresponding to a different predetermined food exchange, wherein such a food exchange corresponds to a predetermined grouping of foodstuffs;

providing memory means for storing numerical values corresponding to a predetermined set of nutritional quantities associated with each food exchange;

providing first calculating means for rendering numerical manipulations in response to manual activation of at least one of said plurality of keys of the first keyboard means;

providing first means for displaying at least two numerical values each corresponding, respectively, to at least two nutritional quantities, wherein one of said nutritional quantities is the approximate cumulative caloric level accumulated since a given starting time;

providing second keyboard means;

configuring the second keyboard means to comprise a plurality of keys;

providing second calculating means for rendering numerical manipulations in response to manual activation of at least one of said plurality of keys of said second keyboard means;

configuring the plurality of keys of the second keyboard means to enter, into said second calculating means, at least a user's weight;

providing second displaying means for displaying at least one numerical value corresponding at least to a recommended daily caloric intake for losing a predetermined amount of weight per week;

said method further comprising the additional steps of:

manually activating one of said plurality of keys of said second keyboard means and entering, into said second calculating means, at least a user's weight;

rendering, with said second calculating means, numerical manipulations in response to the manual activation of the one of said plurality of keys of said second keyboard means;

displaying, with said second displaying means, at least one numerical value corresponding at least to a recommended daily caloric intake for losing a predetermined amount of weight per week;

storing, with said memory means, numerical values corresponding to a predetermined set of nutritional quantities associated with a predetermined food exchange;

manually activating one of said plurality of keys of said first keyboard means corresponding to the predetermined food exchange;

rendering, with said first calculating means, numerical manipulations in response to the manual activation of the one of said plurality of keys of said first keyboard means; and displaying, with said first displaying means, at least two numerical values each corresponding, respectively, to at least two nutritional quantities, wherein one of said nutritional quantities is the approximate cumulative caloric level accumulated since a given starting time.

3. A device for rendering numerical manipulations of data relating to personal nutrition, said device comprising:

keyboard means comprising a plurality of keys, each of said plurality of keys corresponding to a different predetermined food exchange, wherein such a food exchange corresponds to a predetermined grouping of foodstuffs;

memory means for storing numerical values corresponding to a predetermined set of nutritional quantities associated with each food exchange;

calculating means for rendering numerical manipulations in response to manual activation of at least one of said plurality of keys;

means for displaying at least two numerical values each corresponding, respectively, to at least two nutritional quantities, wherein one of said nutritional quantities is the approximate cumulative caloric level accumulated since a given starting time;

said device being manually portable, manually operable and manually holdable;

a second one of said at least two nutritional quantities being a percentage value of the displayed cumulative caloric level accounted for by total fat;

a third one of said at least two nutritional quantities being a percentage value of the displayed cumulative caloric level accounted for by one of: protein and carbohydrates;

a fourth one of said at least two nutritional quantities being a percentage value of the displayed cumulative caloric level accounted for by the other of: protein and carbohydrates;

said calculating means being a first calculating means;

said device further comprising second calculating means, said second calculating means having means for rendering numerical manipulations;

said keyboard means being a first keyboard means;

said device further comprising second keyboard means, said second keyboard means having a plurality of manually activated keys;

said first calculating means being contained within said first keyboard means;

said second calculating means being contained within said second keyboard means;

said device further comprising means for connecting said first keyboard means and said second keyboard means with one another to simultaneously render said first keyboard means and said second keyboard means available to a user at a given time;

each of said plurality of keys of said second keyboard means being configured to enter, into said second calculating means, at least a user's weight;

said means for rendering numerical manipulations of said second calculating means having means for rendering numerical manipulations in response to manual activation of at least one of said plurality of keys of said second keyboard means;

said displaying means being a first displaying means; and said device further comprising second displaying means, said second displaying means having means for displaying at least one numerical value corresponding at least to a recommended daily caloric intake for losing a predetermined amount of weight per week.

* * * * *